(12) United States Patent  (10) Patent No.: US 8,710,459 B1
Davis, III  (45) Date of Patent: Apr. 29, 2014

(54) UV LIQUID TREATMENT SYSTEM

(71) Applicant: Thomas W. Davis, III, Bethany, LA (US)

(72) Inventor: Thomas W. Davis, III, Bethany, LA (US)

( * ) Notice: Subject to any disclaimer, the term of this patent is extended or adjusted under 35 U.S.C. 154(b) by 0 days.

(21) Appl. No.: 13/868,799

(22) Filed: Apr. 23, 2013

(51) Int. Cl.
*C02F 1/00* (2006.01)
*C02F 9/00* (2006.01)
*C02F 1/32* (2006.01)

(52) U.S. Cl.
CPC ............... *C02F 1/325* (2013.01); *C02F 9/005* (2013.01)
USPC ............... 250/455.11; 250/504 R; 250/436; 250/425; 250/435; 422/186.3; 422/24; 210/440; 210/748.1

(58) Field of Classification Search
CPC ................................. C02F 1/325; C02F 9/005
USPC ............... 250/504 R, 455.11, 436, 428, 435; 422/186.3, 24; 210/440, 748.1
See application file for complete search history.

(56) References Cited

U.S. PATENT DOCUMENTS

| | | | | |
|---|---|---|---|---|
| 3,923,663 | A * | 12/1975 | Reid | 210/251 |
| 4,201,917 | A * | 5/1980 | Graentzel | 250/431 |
| 4,535,247 | A | 8/1985 | Kurtz | |
| 4,615,799 | A | 10/1986 | Mortensen | |
| 4,857,204 | A * | 8/1989 | Joklik | 210/695 |
| 4,911,212 | A * | 3/1990 | Burton | 141/369 |
| 4,971,687 | A * | 11/1990 | Anderson | 210/85 |
| 5,780,860 | A | 7/1998 | Gadgil et al. | |
| 5,874,741 | A | 2/1999 | Matschke | |
| 6,461,520 | B1 | 10/2002 | Engelhard et al. | |
| 6,569,319 | B2 | 5/2003 | Kuennen et al. | |
| 6,797,970 | B1 * | 9/2004 | Gatter et al. | 250/504 R |
| 6,946,651 | B1 | 9/2005 | Bohne | |
| 7,089,763 | B2 | 8/2006 | Forsberg et al. | |
| 7,169,311 | B2 | 1/2007 | Saccomanno | |
| 7,361,904 | B2 | 4/2008 | Cassassuce et al. | |
| 7,396,459 | B2 * | 7/2008 | Thorpe | 210/205 |
| 7,476,870 | B2 * | 1/2009 | Hopaluk et al. | 250/436 |
| 7,534,356 | B2 | 5/2009 | Saccomanno | |
| 7,741,617 | B2 * | 6/2010 | Matthews et al. | 250/455.11 |
| 7,838,845 | B2 * | 11/2010 | Abe et al. | 250/432 R |
| 8,017,921 | B2 | 9/2011 | Kemp et al. | |
| 2008/0067414 | A1 | 3/2008 | Cassassuce et al. | |
| 2009/0095691 | A1 * | 4/2009 | Thorpe | 210/748 |
| 2010/0090840 | A1 | 4/2010 | Schreiner | |
| 2011/0024646 | A1 * | 2/2011 | Abe et al. | 250/436 |
| 2011/0104017 | A1 | 5/2011 | Migliore et al. | |
| 2012/0241644 | A1 * | 9/2012 | Ben-David et al. | 250/436 |

* cited by examiner

*Primary Examiner* — David A Vanore
(74) *Attorney, Agent, or Firm* — R. Keith Harrison

(57) ABSTRACT

A UV liquid treatment system comprises least one UV treatment unit including a unit container having a container interior; a liquid distribution head carried by the unit container; at least one liquid inlet passage in the liquid distribution head and disposed in fluid communication with the unit container interior of the unit container; at least one liquid outlet passage in the liquid distribution head and disposed in fluid communication with the unit container interior of the unit container; a transparent light bulb shield carried by the liquid distribution head and having a shield interior; an assembly cavity in the liquid distribution head and communicating with the shield interior of the light bulb shield; a UV light assembly having a UV light bulb removably seated in the assembly cavity, the UV light bulb disposed in the shield interior of the light bulb shield; and a power source electrically connected to the UV light bulb of the UV light assembly.

20 Claims, 6 Drawing Sheets

UV LIQUID TREATMENT SYSTEM

FIELD

Illustrative embodiments of the disclosure generally relate to antimicrobial treatment of water and other liquids. More particularly, illustrative embodiments of the disclosure relate to a UV liquid treatment system which utilizes ultraviolet radiation to neutralize microorganisms in water or other liquid, is adaptable to a variety of liquid treatment systems and can be easily maintained.

BACKGROUND

Water from lakes, rivers and other natural water bodies may contain microorganisms which must be neutralized (removed, killed and/or rendered non-reproducible) to render the water potable or useful for some other purpose. Examples of microorganisms which may be present in water from natural sources include bacteria such as *campylobacter, cryptosporidium, escherichia coli (E-coli), salmonella* and *shigella*. These microorganisms may cause cholera, diarrhea and other illnesses in persons who consume water in which they thrive if the water is not properly sanitized before consumption. Therefore, various techniques have been used to render natural water or other liquid potable or useful for some other purpose by neutralizeneutralizing harmful microorganisms from the water.

A UV liquid treatment system which utilizes ultraviolet radiation to neutralize microorganisms in water or other liquid, is adaptable to a variety of liquid treatment systems and can be easily maintained may be desirable for some applications.

SUMMARY

Illustrative embodiments of the disclosure are generally directed to a UV liquid treatment system which utilizes ultraviolet radiation to neutralizemicroorganisms in water or other liquid, is adaptable to a variety of liquid treatment systems and can be easily maintained. An illustrative embodiment of the UV liquid treatment system comprises least one UV treatment unit including a unit container having a container interior; a liquid distribution head carried by the unit container; at least one liquid inlet passage in the liquid distribution head and disposed in fluid communication with the unit container interior of the unit container; at least one liquid outlet passage in the liquid distribution head and disposed in fluid communication with the unit container interior of the unit container; a transparent light bulb shield carried by the liquid distribution head and having a shield interior; an assembly cavity in the liquid distribution head and communicating with the shield interior of the light bulb shield; a UV light assembly having a UV light bulb removably seated in the assembly cavity, the UV light bulb disposed in the shield interior of the light bulb shield; and a power source electrically connected to the UV light bulb of the UV light assembly.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is non-limiting and is not necessarily to be construed as preferred or advantageous over other implementations. All of the implementations described below are exemplary implementations provided to enable persons skilled in the art to practice the disclosure and are not intended to limit the scope of the appended claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. Relative terms such as "upper", "lower", "above", "below", "top", "bottom", "interior", "exterior", "outer", "horizontal" and "vertical" as used herein are intended for descriptive purposes only and relate to typical positions of the so-labeled components in exemplary use of the UV liquid treatment system. Such relative terms are not necessarily intended to be construed in a limiting sense.

Figure 1:
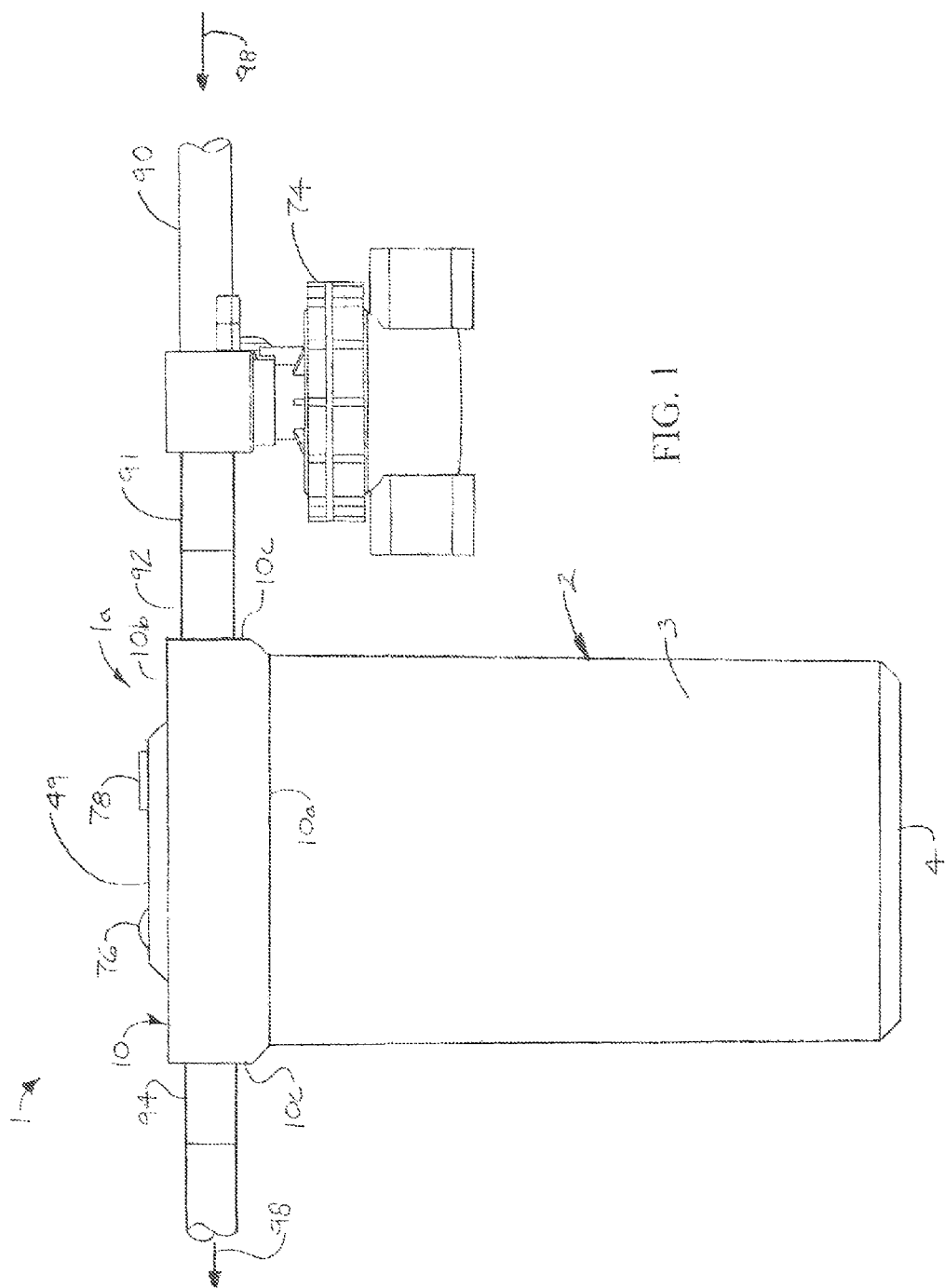
FIG. 1 is a side view, partially in section, of an illustrative embodiment of a UV liquid treatment system.
Figure 2:
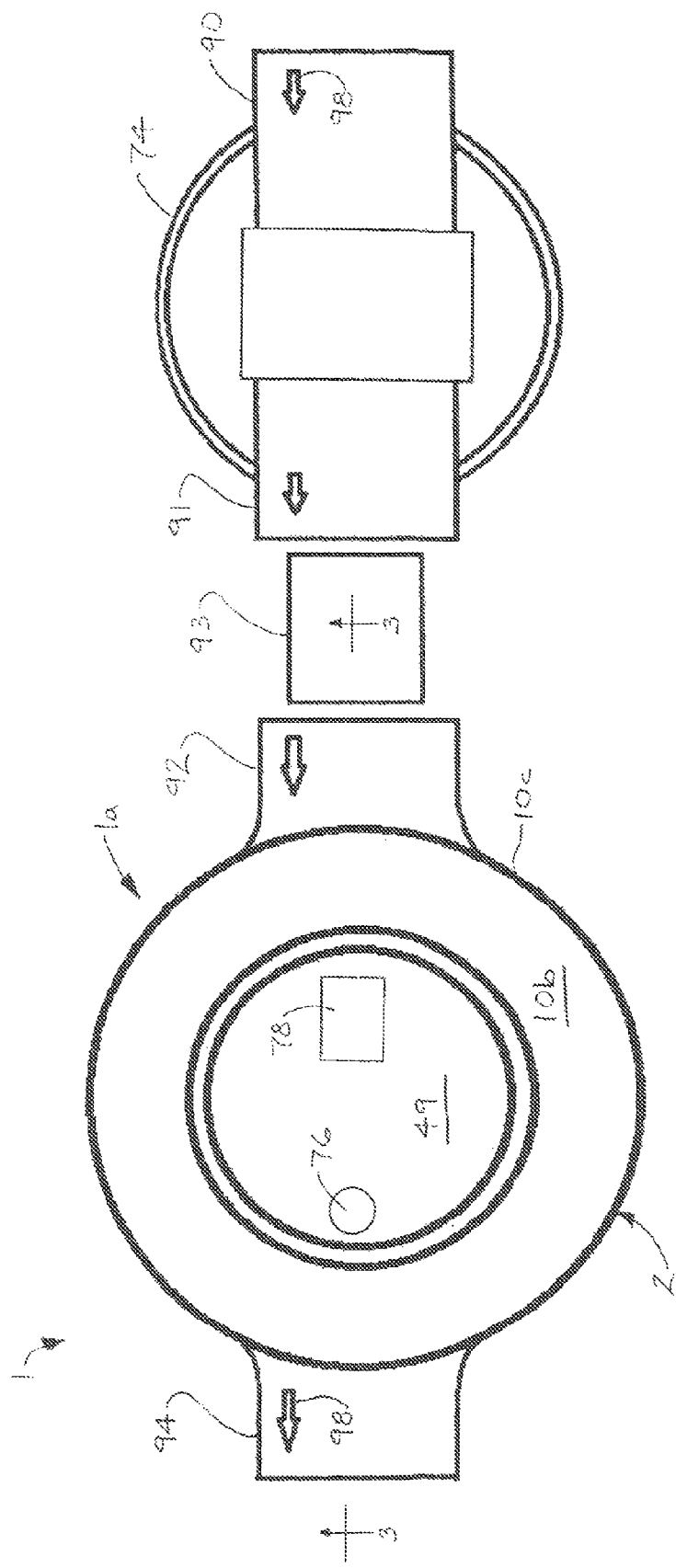
FIG. 2 is an exploded top view of an illustrative embodiment of a UV liquid treatment system.

Referring to the drawings, an illustrative embodiment of the UV liquid treatment system, hereinafter system, is generally indicated by reference numeral 1. As illustrated in FIGS. 1 and 2, the system 1 includes at least one UV treatment unit 1a. The system 1 may further include at least one shutoff valve 74 which is disposed in fluid communication with the UV treatment unit la. In exemplary application of the system 1, which will be hereinafter described, a liquid 98 such as water obtained from a lake, river or other natural water body, for example and without limitation, is distributed through the shutoff valve 74 and the UV treatment unit 1a, respectively, of the system 1. As it passes through the UV treatment unit 1a, the liquid 98 is subjected to ultraviolet light 59 (FIG. 3) which neutralizes microorganisms in the liquid 98 to render the liquid 98 potable or useful for some other purpose.

Figure 6:
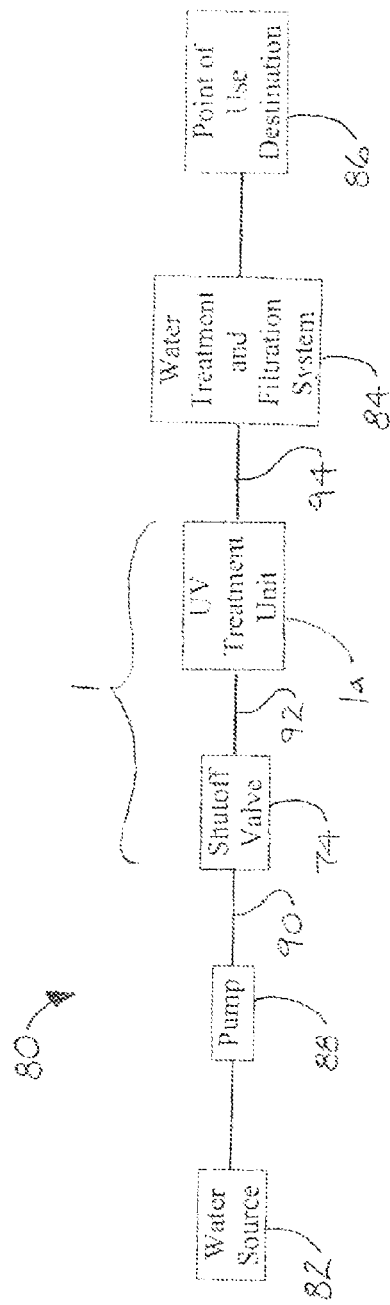
FIG. 6 is a block diagram of a multi-stage water treatment system which utilizes an illustrative embodiment of the UV liquid treatment system in the treatment of water from a natural water source according to exemplary application of the UV liquid treatment system.

In some applications, the system 1 may be used alone or in combination with other components which remove the neutralized microorganisms and other impurities from the liquid 98. For example and without limitation, as illustrated in FIG. 6, in some applications, the system 1 may operate as a component part of a multi-stage liquid treatment system 80 which utilizes UV light treatment in addition to other purifying methods or techniques to purify the liquid 98. In some applications, the multi-stage liquid treatment system 80 may be adapted to purify liquid 98 in the form of water which is distributed from a water source 82 such as a lake or river, for example and without limitation. The multi-stage liquid treatment system 80 may include at least one pump 88 which is disposed in fluid communication with the water source 82. The system 1 may include the shutoff valve 74, which communicates with the pump 88 and the UV treatment unit 1a which communicates with the shutoff valve 74. A water treatment and filtration system 84 may communicate with the UV treatment unit 1a. At least one point of use destination 86 may communicate with the water treatment and filtration system 84. The point of use destination 86 may include at least one home or business which receives the purified liquid water from the water treatment and filtration system 84 for drinking and/or other purposes.

Figure 3:
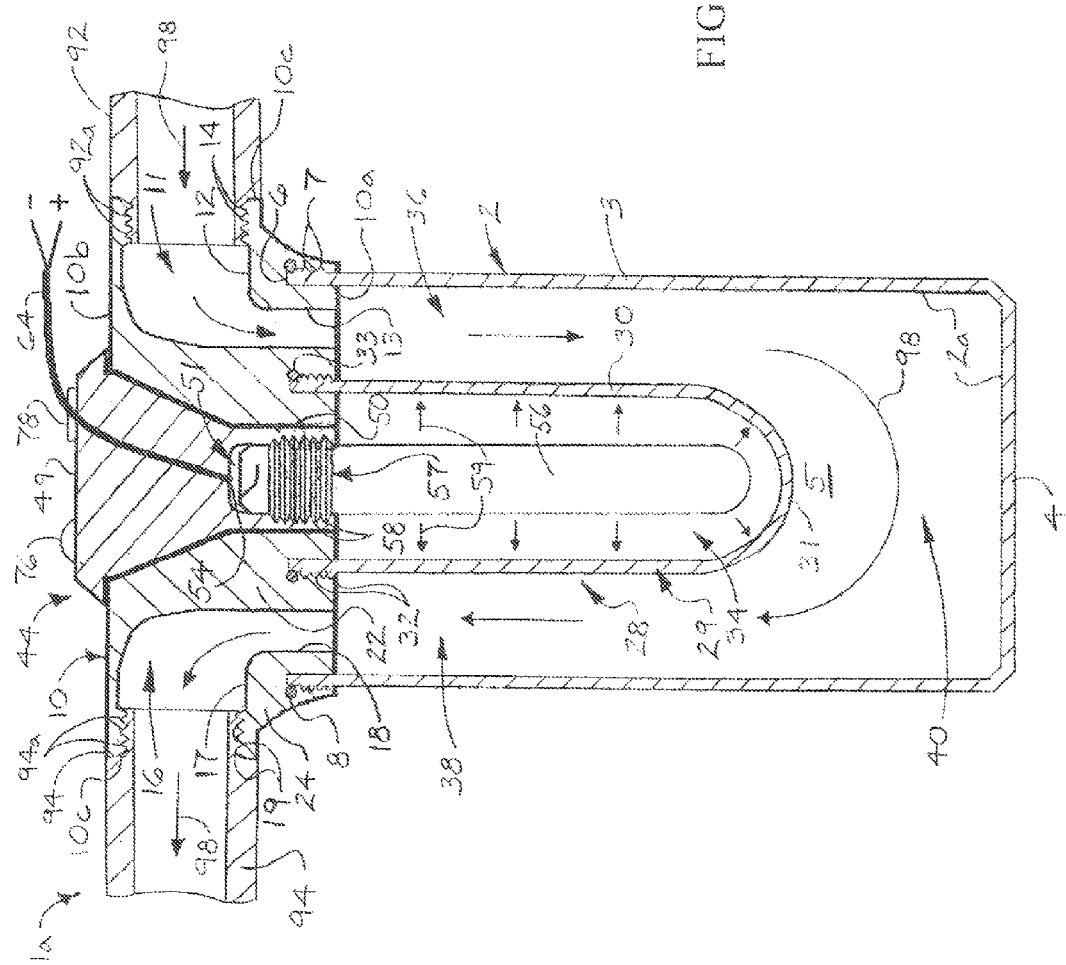
FIG. 3 is a longitudinal sectional view, taken along section lines 3-3 in FIG. 2, of an exemplary UV treatment unit of an illustrative embodiment of a UV liquid treatment system.
Figure 3A:
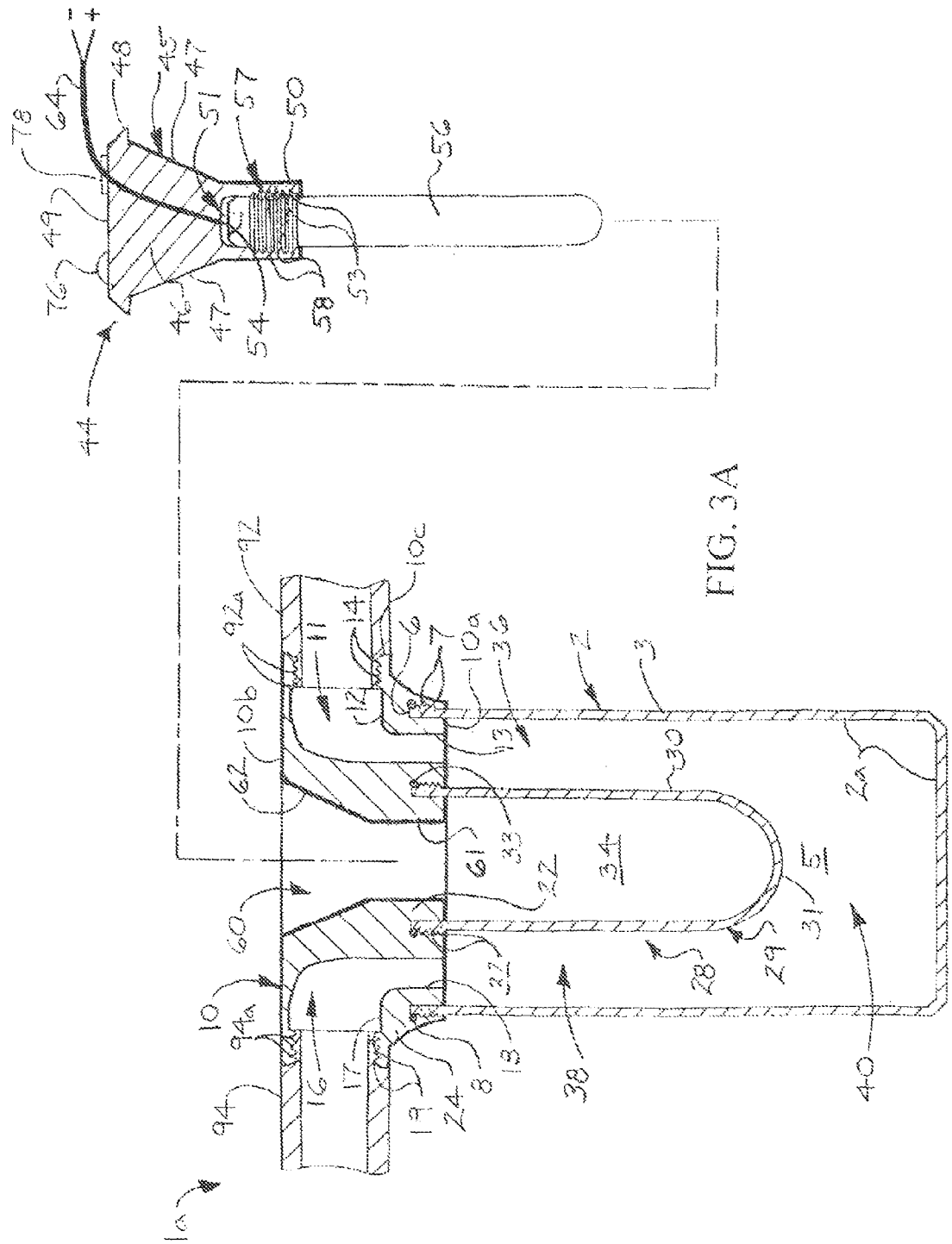
FIG. 3A is an exploded longitudinal sectional view of an exemplary UV treatment unit, with an exemplary UV light assembly removed from the UV treatment unit for replacement of a UV light bulb in the UV light assembly.

As illustrated in FIGS. 3 and 3A, the UV treatment unit 1a of the system 1 includes a unit container 2. In some embodiments, the unit container 2 may include a container sidewall 3, a container bottom 4 which closes the bottom of the container sidewall 3 and a container interior 5. The container sidewall 3 may have a container sidewall edge 6. Container threads 7 may be provided in the container sidewall 3 generally at or adjacent to the container sidewall edge 6 for purposes which will be hereinafter described. The unit container 2 may be cylindrical or non-cylindrical in shape and the container sidewall 3 and container bottom 4 may be plastic, metal and/or other material which is consistent with the functional requirements of the unit container 2. In some embodiments, a light-reflective surface 2a may be provided on the interior surfaces of the unit container 2.

Figure 4:
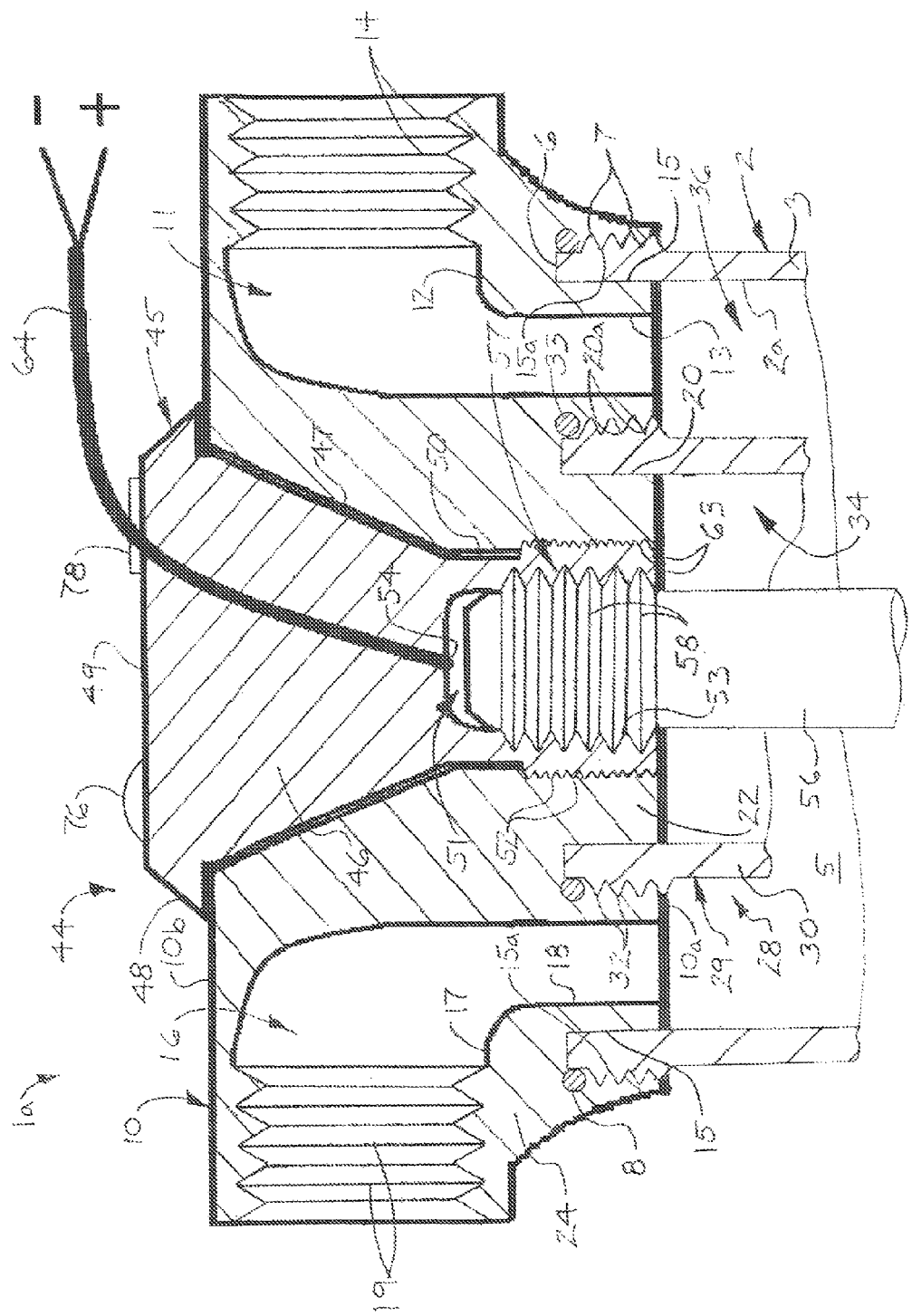
FIG. 4 is an enlarged sectional view of an exemplary liquid distribution head of the UV treatment unit.

A liquid distribution head 10 is provided on the unit container 2. The liquid distribution head 10 may generally include a center head portion 22 and an outer head portion 24 which extends outwardly from the center head portion 22. As illustrated in FIGS. 3, 3A and 4, the liquid distribution head 10 may further have an interior head surface 10a which faces the container interior 5 of the unit container 2, an exterior head surface 10b which is opposite the interior head surface 10a and an outer head surface 10c which extends between the interior head surface 10a and the outer head surface 10b. At least one liquid inlet passage 11 may include a primary inlet passage segment 12 which extends horizontally from the outer head surface 10c through the outer head portion 24 toward the center head portion 22 and a secondary inlet passage segment 13 which communicates with and is perpendicular to the primary inlet passage segment 12 and opens to the interior head surface 10a. At least one liquid outlet passage 16 may include a primary outlet passage segment 17 which extends horizontally from the outer head surface 10c through the outer head portion 24 toward the center head portion 22 and a secondary outlet passage segment 18 which communicates with and is perpendicular to the primary outlet passage segment 17 and opens to the interior head surface 10a. In some embodiments, the liquid inlet passage 11 and the liquid outlet passage 16 may be disposed generally in diametrically-opposed or 180-degree relationship to each other on opposite sides of the liquid distribution head 10. The liquid inlet passage 11 and the liquid outlet passage 16 may generally demarcate the outer head portion 24 from the center head portion 22. In some embodiments, inlet passage threads 14 may be provided in the primary inlet passage segment 12 of the liquid inlet passage 11 and outlet passage threads 19 may be provided in the primary outlet passage segment 17 of the liquid outlet passage 16 for purposes which will be hereinafter described. As illustrated in FIG. 3A, a assembly cavity 60 may extend through the center head portion 22 from the interior head surface 10a to the exterior head surface 10b for purposes which will be hereinafter described.

The unit container 2 may be attached to the liquid distribution head 10 according to any suitable technique which is known by those skilled in the art. As illustrated in FIG. 4, in some embodiments, an annular container slot 15 may extend into the interior head surface 10a at the outer head portion 24 of the liquid distribution head 10. Container slot threads 15a may extend into the container slot 15. The container threads 7 on the container sidewall 3 of the unit container 2 may threadably engage the companion container slot threads 15a in the container slot 15 as the unit container 2 is rotated to detachably secure the unit container 2 to the liquid distribution head 10. A container seal 8, such as an O-ring, for example and without limitation, in the outer head portion 24 of the liquid distribution head 10 may sealingly engage the container sidewall 3 of the unit container 2 to provide a liquid-tight seal between the container interior 5 of the unit container 2 and the liquid distribution head 10.

A light bulb shield 28 extends from the center head portion 22 of the liquid distribution head 10 into the container interior 5 of the unit container 2. The light bulb shield 28 may include a shield wall 29 which is transparent glass or plastic and encloses a shield interior 34. The shield wall 29 of the light bulb shield 28 may include a generally elongated main wall portion 30 and a bottom wall portion 31 which closes the main wall portion 30.

The light bulb shield 28 may be sealingly attached to the liquid distribution head 10 according to any suitable technique which is known by those skilled in the art. In some embodiments, an annular shield slot 20 (FIG. 4) may extend into the interior head surface 10a at the center head portion 22 of the liquid distribution head 10. Shield slot threads 20a may extend into the shield slot 20. The shield threads 32 on the main wall portion 30 of the light bulb shield 28 may threadably engage the companion shield slot threads 20a in the shield slot 20 of the liquid distribution head 10 to detachably secure the light bulb shield 28 to the liquid distribution head 10. A shield seal 33, such as an O-ring, for example and without limitation, in the inner head portion 22 of the liquid distribution head 10 may sealingly engage the shield wall 29 of the light bulb shield 28 to impart a liquid-tight seal between the shield interior 34 of the light bulb shield 28 and the container interior 5 of the unit container 2.

As illustrated in FIGS. 3 and 3A, a descending liquid flow passage 36 and an ascending liquid flow passage 38 are formed by and between the main wall portion 30 of the light bulb shield 28 and the container sidewall 3 of the unit container 2. The descending liquid flow passage 36 is disposed in fluid communication with the liquid inlet passage 11. The ascending liquid flow passage 38 is disposed in fluid communication with the liquid outlet passage 16. The descending liquid flow passage 36 and the ascending liquid flow passage 38 are semi-annular and communicate with each other to form a continuous annular space around the light bulb shield 28. A transition space 40 is formed by and between the bottom wall portion 31 of the light bulb shield 28 and the container bottom 4 of the unit container 2. The transition space 40 establishes fluid communication between the descending liquid flow passage 36 and the ascending liquid flow passage 38 in the lower portion of the container interior 5.

As illustrated in FIGS. 3, 3A and 4, a removable UV light assembly 44 is seated in the assembly cavity 60 (FIG. 3A) in the liquid distribution head 10. As illustrated in FIG. 3A, the UV light assembly 44 may have a receptacle plug 45 which may include rubber, plastic, metal and/or other material. The receptacle plug 45 may include a receptacle plug body 46. An outwardly-flared plug head 48 having a plug head surface 49 may be provided on the receptacle plug body 46. A generally cylindrical light bulb receptacle 50 having a receptacle cavity 51 extends from the receptacle plug body 46. The receptacle plug 45 may have a tapered body surface 47 which tapers from the plug head 48 to the light bulb receptacle 50. As illustrated in FIG. 4, the receptacle cavity 51 of the light bulb receptacle 50 has interior receptacle threads 53. A UV light bulb 56 has a light bulb base 57 with socket threads 58 which engage the companion receptacle threads 53 in the light bulb receptacle 50. An electrical contact 54 is provided in the receptacle cavity 51. Light bulb wiring 64 electrically connects the electrical contact 54 to a power source 70 (FIG. 5) such as an AC power source, for example and without limitation. Accordingly, the UV light bulb 56 is energized and illuminated by physical contact of the light bulb base 57 with the electrical contact 54 when the light bulb base 57 is threaded in the receptacle cavity 51 of the light bulb receptacle 50.

As illustrated in FIG. 3A, in some embodiments, the assembly cavity 60 may include a straight cavity portion 61 which opens to the interior head surface 10a and a tapered cavity portion 62 which communicates with the straight cavity portion 61 and opens to the exterior head surface 10b. Accordingly, the receptacle plug 45 of the UV light assembly 44 can be selectively seated in the assembly cavity 60 such that the tapered body surface 47 of the receptacle plug body 46 engages the tapered cavity portion 62 of the assembly cavity 60 and the light bulb receptacle 50 of the receptacle plug 45 engages the straight cavity portion 61 of the assembly cavity 60. The plug head 48 of the receptacle plug 45 seats against the exterior head surface 10b of the liquid distribution head 10. In some embodiments, the receptacle plug 45 of the UV light assembly 44 may include an elastomeric material such as rubber and/or plastic. Accordingly, the receptacle plug 45 may seat in the assembly cavity 60 under the weight of the UV light assembly 44 or may be deformed by close tolerances of the assembly cavity 60 and secured therein via an interference fit. As illustrated in FIG. 4, in some embodiments, the light bulb receptacle 50 may have exterior plug attachment threads 52 which engage companion interior cavity threads 63 to additionally or alternatively secure the receptacle plug 45 of the UV light assembly 44 in the assembly cavity 60. The UV light bulb 56 extends downwardly into the shield interior 34 of the light bulb shield 28, which forms a liquid-tight seal between the UV light bulb 56 and the container interior 5 of the unit container 2.

It will be appreciated by those skilled in the art that a burned-out or otherwise inoperable UV light bulb 56 can be easily and expeditiously replaced, as deemed necessary, by removal of the receptacle plug 45 of the UV light assembly 44 from the assembly cavity 60 in the liquid distribution head 10, as illustrated in FIG. 3A; unthreading the light bulb base 57 of the UV light bulb 56 from the light bulb receptacle 50; threading the light bulb base 57 of a replacement UV light bulb 56 into the light bulb receptacle 50; and re-inserting or seating the receptacle plug 45 in the assembly cavity 60 with the replacement UV light bulb 56 extending into the shield interior 34 of the light bulb shield 28.

Figure 5:
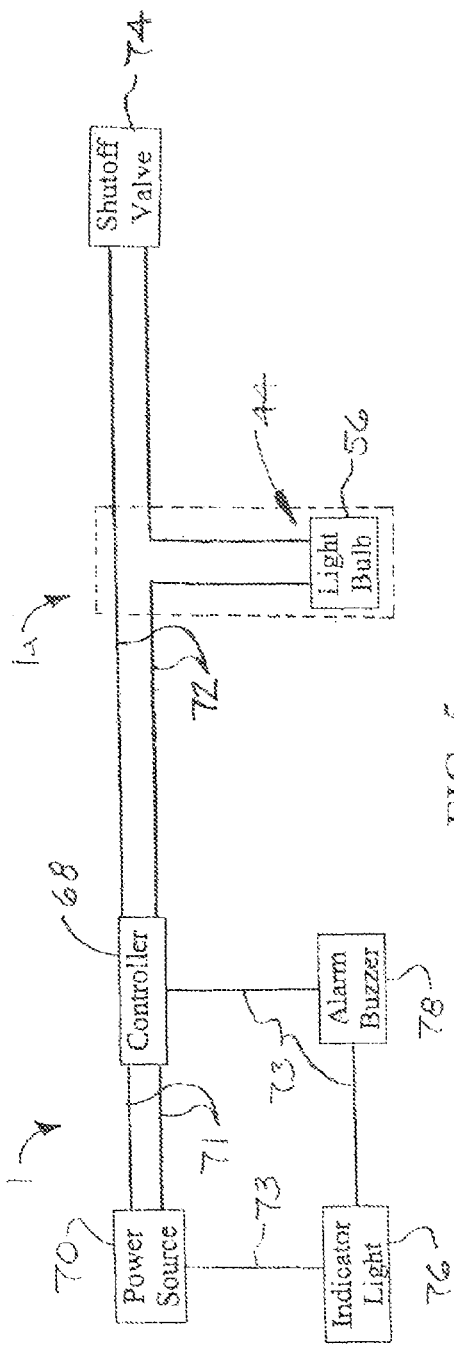
FIG. 5 is a functional block diagram of an illustrative embodiment of a UV liquid treatment system.

As illustrated in FIG. 5 of the drawings, in some embodiments, the system 1 may include a controller 68 which is electrically connected to the power source 70 via electrical connections 71. The UV light bulb 56 of the UV light assembly 44, and the shutoff valve 74, may be electrically connected to the controller 68 via electrical connections 72. At least one of an indicator light 76 and an alarm buzzer 78 may be electrically connected to the controller 68 and the power source 70 via electrical connections 73. The indicator light 76 and/or the alarm buzzer 78 may be placed in any suitable location which renders the indicator light 76 and the alarm buzzer 78 visible and audible, respectively, to an operator of the system 1. For example and without limitation, in some embodiments, the indicator light 76 and/or the alarm buzzer 78 may be placed on the plug head surface 49 on the receptacle plug 45 of the UV light assembly 44, as illustrated in FIGS. 1-4.

In the event that the UV light bulb 56 of the UV light assembly 44 inadvertently burns out or is otherwise inadvertently rendered non-functional, the controller 68 may be programmed to close the shutoff valve 74, which terminates further flow of the liquid 98 through the UV treatment unit 1a. Additionally, the controller 68 is adapted to operate at least one of the indicator light 76 and the alarm buzzer 78 which indicates the nonfunctional operational status of the UV light bulb 56. The controller 68 may be adapted to open the shutoff valve 74 to resume flow of the liquid through the UV liquid treatment system 1a upon repair or replacement of the UV light bulb 56. For example and without limitation, in some embodiments, a reset switch (not illustrated) or the like which interfaces with the controller 68 may be manipulated to reset the indicator light 76 and/or the alarm buzzer 78 to resume operation of the system 1.

As illustrated in FIGS. 5 and 6 of the drawings, in exemplary application, the system 1 may operate as part of a multi-stage liquid treatment system 80 to neutralize and remove microorganisms and other impurities from liquid 98 such as water from a lake, river or other natural water source 82, for example and without limitation. However, it will be recognized and understood that in other applications the system 1 may operate independently of a multi-stage system 80 to neutralize microorganisms in the liquid 98 for any of a variety of purposes. In the multi-stage liquid treatment system 80, at least one pump 88 may communicate with the water source 82. The shutoff valve 74 of the system 1 may communicate with the pump 88 through a valve inlet conduit 90. The UV treatment unit 1a of the system 1 may communicate with the shutoff valve 74 through a valve outlet conduit 91 and a system inlet conduit 92 (FIG. 2). A water treatment and filtration system 84 may communicate with the UV treatment unit 1a of the system 1 through a system outlet conduit 94. The water treatment and filtration system 84 may include at least one filter (not illustrated) which removes particulate matter from the liquid 98 as the liquid 98 passes through the water treatment and filtration system 84. At least one point of use destination 86 may communicate with the water treatment and filtration system 84. The point of use destination 86 may include at least one home or business which receives purified water from the water treatment and filtration system 84 for drinking and/or other purposes.

As illustrated in FIG. 2, in some embodiments, the valve outlet conduit 91 of the shutoff valve 74 may be connected to the system inlet conduit 92 of the UV treatment unit 1a by inserting a conduit sleeve 93 into the valve outlet conduit 91 and the system inlet conduit 92. The valve outlet conduit 91 and the system inlet conduit 92 may be attached to the conduit sleeve 93 using glue, mechanical fasteners, via a friction or interference fit and/or other suitable attachment techniques known by those skilled in the art. It will be recognized and understood that various other attachment techniques may be used to connect the shutoff valve 74 in fluid communication with the UV treatment unit 1a. As illustrated in FIGS. 3 and 3A, the system inlet conduit 92 may be attached to the liquid distribution head 10 and in fluid communication with the liquid inlet passage 11 by engagement of conduit threads 92a on the system inlet conduit 92 with companion inlet passage threads 14 in the liquid inlet passage 14. The system outlet conduit 94 may be attached to the liquid distribution head 10 in fluid communication with the liquid outlet passage 16 by engagement of conduit threads 94a on the system outlet conduit 94 with companion outlet passage threads 19 in the liquid outlet passage 16.

Under normal operating conditions, the controller 68 (FIG. 5) maintains the shutoff valve 74 in an open operational position. The pump 88 pumps the liquid 98 from the water source 82 through the open shutoff valve 74 and the UV treatment unit 1a, respectively, of the system 1. Accordingly, the liquid 98 flows from the shutoff valve 74 through the system inlet 92 and the liquid inlet passage 11 (FIG. 3) of the liquid distribution head 10 and then through the descending liquid flow passage 36, the transition space 40 and the ascending liquid fluid passage 38, respectively, in the container interior 5 of the unit container 2. The flowing liquid 98 exits the container interior 5 through the liquid outlet passage 16 in the liquid distribution head 10 and the system outlet conduit 94, respectively, and may then flow to the water treatment and filtration system 84 where additional filtering and treatment of the liquid 98 may be carried out. Finally, the purified liquid 98 may be distributed from the water treatment and filtration system 84 to the point of use destination 86 for use or consumption.

Throughout operation of the UV liquid treatment system 1, the controller 68 (FIG. 5) energizes the UV light bulb 56, which emits UV light 59 (FIG. 3) through the light bulb shield 28 into the container interior 5 and through the flowing liquid 98. In some embodiments, the UV light 59 may be intensified as it reflects back from the interior light reflective surfaces 2a (FIG. 3) of the unit container 2 through the liquid 98 as the liquid 98 passes through the container interior 5. Accordingly, the UV light 59 neutralizes bacteria, algae and other microorganisms in the liquid 98 such that the liquid 98 is substantially free of living microorganisms as the liquid 98 emerges from the UV treatment unit 1a through the system outlet conduit 94. It will be appreciated by those skilled in the art that the semi-annular shape of each of the descending liquid flow passage 36 and the ascending liquid flow passage 38, in combination with the transition space 40, enables a large volume of the liquid 98 to be treated as it passes through the container interior 5.

In the event that the UV light bulb 56 burns out or is otherwise rendered non-functional during operation of the system 1, the controller 68 (FIG. 5) closes the shutoff valve 74. Therefore, further flow of the liquid 98 through the system 1 and the water treatment and filtration system 84 to the point of use destination 86 of the multi-stage treatment system 80 is terminated. The controller 68 may additionally energize at least one of the indicator light 76 and the alarm buzzer 78, which indicates to personnel that the UV light bulb 44 requires replacement.

As illustrated in FIG. 3A, the UV light assembly 44 can be selectively removed from the liquid distribution head 10 for replacement of the UV light bulb 56 by disengaging and removing the receptacle plug 45 of the UV light assembly 44 from the assembly cavity 60 in the liquid distribution head 10. In some embodiments, this may be accomplished by initially rotating the receptacle plug 45 to disengage the plug attachment threads 52 (FIG. 4) from the companion cavity threads 63 and then lifting the receptacle plug 45 from the assembly cavity 60. The burned-out or nonfunctional UV light bulb 56 may be unthreaded from the light bulb receptacle 50 and a replacement UV light bulb 56 threaded in its place in the light bulb receptacle 50. The UV light assembly 44 is then replaced in the liquid distribution head 10 by inserting and seating the receptacle plug 45 back in the assembly cavity 60 with the UV light bulb 56 extending into the shield interior 34 of the light bulb shield 28. In some embodiments, a reset switch (not illustrated) or the like which interfaces with the controller 68 may be manipulated to turn off the indicator light 76 and/or the alarm buzzer 78 to resume operation of the system 1.

Referring again to FIG. 6 of the drawings, in some applications, the system 1 may be placed between the water treatment and filtration system 84 and the point of use destination 86. For example and without limitation, in some applications the water treatment and filtration system 84 may be a municipal water treatment system The system 1 may be connected to the water supply of a home or business beneath a kitchen or bathroom sink, for example and without limitation, to neutralize microorganisms in water before the water is dispensed from a faucet for consumption or use. It will be appreciated by those skilled in the art that in some applications, the system 1 may be fabricated in a variety of sizes for different applications.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. A UV liquid treatment system, comprising:
   at least one UV treatment unit including:
      a unit container having a container sidewall, a container bottom extending from the container sidewall and a container interior formed by and between the container sidewall and the container bottom;
      a liquid distribution head carried by the unit container;
      at least one liquid inlet passage in the liquid distribution head and disposed in fluid communication with the unit container interior of the unit container;
      at least one liquid outlet passage in the liquid distribution head and disposed in fluid communication with the unit container interior of the unit container, the at least one liquid inlet passage and the at least one liquid outlet passage disposed generally in 180-degree relationship to each other on opposite sides of the liquid distribution head;
      a transparent light bulb shield carried by the liquid distribution head and having a shield interior;
      a descending liquid flow passage formed by and between the light bulb shield and the container sidewall of the unit container, the descending liquid flow passage disposed in fluid communication with the at least one liquid inlet passage;
      a transition space formed by and between the light bulb shield and the container bottom of the unit container, the transition space disposed in fluid communication with the descending liquid flow passage;
      an ascending liquid flow passage formed by and between the light bulb shield and the container sidewall of the unit container, the ascending liquid flow passage disposed in fluid communication with the transition space and the at least one liquid outlet passage;
      an assembly cavity in the liquid distribution head and communicating with the shield interior of the light bulb shield;
      a UV light assembly having a UV light bulb removably seated in the assembly cavity, the UV light bulb disposed in the shield interior of the light bulb shield; and
      a power source electrically connected to the UV light bulb of the UV light assembly.

2. The UV liquid treatment system of claim 1 wherein the UV light assembly comprises a receptacle plug seated in the assembly cavity and wherein the UV light bulb is carried by the receptacle plug.

3. The UV liquid treatment system of claim 2 wherein the receptacle plug comprises a receptacle plug body, a plug head carried by the receptacle plug body and a light bulb receptacle carried by the receptacle plug body, and wherein the UV light bulb is carried by the light bulb receptacle.

4. The UV liquid treatment system of claim 3 wherein the receptacle plug comprises a tapered body surface tapering from the plug head to the light bulb receptacle.

5. The UV liquid treatment system of claim 4 wherein the assembly cavity comprises a straight cavity portion and a tapered cavity portion communicating with the straight cavity portion, and wherein the light bulb receptacle of the receptacle plug is seated in the straight body portion and the receptacle plug body of the receptacle plug is seated in the tapered cavity portion of the assembly cavity.

6. The UV liquid treatment system of claim 5 wherein the receptacle plug body of the receptacle plug comprises an elastomeric material.

7. The UV liquid treatment system of claim 1 wherein the at least one liquid inlet passage comprises a primary inlet passage segment and a secondary inlet passage segment perpendicular to and communicating with the primary inlet passage segment and the container interior of the unit container.

8. The UV liquid treatment system of claim 1 wherein the at least one liquid outlet passage comprises a primary outlet passage segment and a secondary outlet passage segment communicating with the primary outlet passage segment and the container interior of the unit container.

9. A UV liquid treatment system, comprising:
at least one UV treatment unit including:
a unit container having a container sidewall, a container bottom extending from the container sidewall and a container interior formed by and between the container sidewall and the container bottom;
a liquid distribution head carried by the unit container;
at least one liquid inlet passage in the liquid distribution head and disposed in fluid communication with the unit container interior of the unit container;
at least one liquid outlet passage in the liquid distribution head and disposed in fluid communication with the unit container interior of the unit container, the at least one liquid inlet passage and the at least one liquid outlet passage disposed generally in 180-degree relationship to each other on opposite sides of the liquid distribution head;
a transparent light bulb shield carried by the liquid distribution head and having a shield interior;
a descending liquid flow passage formed by and between the light bulb shield and the container sidewall of the unit container, the descending liquid flow passage disposed in fluid communication with the at least one liquid inlet passage;
a transition space formed by and between the light bulb shield and the container bottom of the unit container, the transition space disposed in fluid communication with the descending liquid flow passage;
an ascending liquid flow passage formed by and between the light bulb shield and the container sidewall of the unit container, the ascending liquid flow passage disposed in fluid communication with the transition space and the at least one liquid outlet passage;
an assembly cavity in the liquid distribution head and communicating with the shield interior of the light bulb shield;
a UV light assembly having a UV light bulb removably seated in the assembly cavity, the UV light bulb disposed in the shield interior of the light bulb shield; and
a power source electrically connected to the UV light bulb of the UV light assembly; and
a shutoff valve disposed in fluid communication with the at least one liquid inlet passage in the liquid distribution head.

10. The UV liquid treatment system of claim 9 wherein the UV light assembly comprises a receptacle plug seated in the assembly cavity and wherein the UV light bulb is carried by the receptacle plug.

11. The UV liquid treatment system of claim 10 wherein the receptacle plug comprises a receptacle plug body, a plug head carried by the receptacle plug body and a light bulb receptacle carried by the receptacle plug body, and wherein the UV light bulb is carried by the light bulb receptacle.

12. The UV liquid treatment system of claim 11 wherein the receptacle plug comprises a tapered body surface tapering from the plug head to the light bulb receptacle.

13. The UV liquid treatment system of claim 12 wherein the assembly cavity comprises, a straight cavity portion and a tapered cavity portion communicating with the straight cavity portion, and wherein the light bulb receptacle of the receptacle plug is seated in the straight body portion and the receptacle plug body of the receptacle plug is seated in the tapered cavity portion of the assembly cavity.

14. The UV liquid treatment system of claim 13 wherein the receptacle plug body of the receptacle plug comprises an elastomeric material.

15. The UV liquid treatment system of claim 9 wherein the at least one liquid inlet passage comprises a primary inlet passage segment and a secondary inlet passage segment perpendicular to and communicating with the primary inlet passage segment and the container interior of the unit container.

16. The UV liquid treatment system of claim 9 wherein the at least one liquid outlet passage comprises a primary outlet passage segment and a secondary outlet passage segment communicating with the primary outlet passage segment and the container interior of the unit container.

17. A UV liquid treatment system, comprising:
at least one UV treatment unit including:
a unit container having a container interior;
a liquid distribution head carried by the unit container;
an assembly cavity extending through the liquid distribution head, the assembly cavity having a straight cavity portion and a tapered cavity portion communicating with the straight cavity portion;
at least one liquid inlet passage in the liquid distribution head and disposed in fluid communication with the unit container interior of the unit container;
at least one liquid outlet passage in the liquid distribution head and disposed in fluid communication with the unit container interior of the unit container;
a transparent light bulb shield carried by the liquid distribution head and having a shield interior;
an assembly cavity in the liquid distribution head and communicating with the shield interior of the light bulb shield;
a UV light assembly having a tapered receptacle plug body seated in the tapered cavity portion of the assembly cavity, a plug head carried by the receptacle plug body and engaging the liquid distribution head, a light bulb receptacle carried by the receptacle plug body and seated in the straight cavity portion of the assembly cavity and a UV light bulb carried by the light bulb receptacle, the UV light bulb disposed in the shield interior of the light bulb shield; and a power source electrically connected to the UV light bulb of the UV light assembly;

a shutoff valve disposed in fluid communication with the at least one liquid inlet passage in the liquid distribution head;

a controller interfacing with the power source, the UV light bulb of the UV light assembly and the shutoff valve; and at least one of an indicator light and an alarm buzzer interfacing with the power source and the controller, the controller adapted to close the shutoff valve and activate the at least one of an indicator light and an alarm buzzer responsive to non-functioning of the UV light bulb of the UV light assembly.

18. The UV liquid treatment system of claim 17 wherein the receptacle plug body of the receptacle plug comprises an elastomeric material.

19. The UV liquid treatment system of claim 17 wherein the at least one liquid inlet passage comprises a primary inlet passage segment and a secondary inlet passage segment perpendicular to and communicating with the primary inlet passage segment and the container interior of the unit container.

20. The UV liquid treatment system of claim 17 wherein the at least one liquid outlet passage comprises a primary outlet passage segment and a secondary outlet passage segment communicating with the primary outlet passage segment and the container interior of the unit container.

* * * * *